(12) United States Patent
Santello

(10) Patent No.: US 11,419,524 B2
(45) Date of Patent: Aug. 23, 2022

(54) REPETITIVE MOTION INJURY WARNING SYSTEM AND METHOD

(71) Applicant: ARIZONA BOARD OF REGENTS ON BEHALF OF ARIZONA STATE UNIVERSITY, Scottsdale, AZ (US)

(72) Inventor: Marco Santello, Gilbert, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 690 days.

(21) Appl. No.: 15/309,641

(22) PCT Filed: May 8, 2015

(86) PCT No.: PCT/US2015/030010
§ 371 (c)(1),
(2) Date: Nov. 8, 2016

(87) PCT Pub. No.: WO2015/172096
PCT Pub. Date: Nov. 12, 2015

(65) Prior Publication Data
US 2017/0265784 A1 Sep. 21, 2017

Related U.S. Application Data

(60) Provisional application No. 61/991,199, filed on May 9, 2014.

(51) Int. Cl.
*A61B 5/11* (2006.01)
*A61B 5/00* (2006.01)

(52) U.S. Cl.
CPC .............. *A61B 5/1121* (2013.01); *A61B 5/11* (2013.01); *A61B 5/7275* (2013.01);
(Continued)

(58) Field of Classification Search
CPC ....... A61B 5/1121; A61B 5/11; A61B 5/7275; A61B 5/7278; A61B 2560/0223; A61B 2562/0219; A61B 2562/0223
See application file for complete search history.

(56) References Cited

U.S. PATENT DOCUMENTS 5,275,174 A     1/1994 Cook
5,474,088 A  *  12/1995 Zaharkin ................ A61B 5/103
                                                           128/897

(Continued)

FOREIGN PATENT DOCUMENTS

WO        2015172096 A1    11/2015

OTHER PUBLICATIONS

Ansell, J. et al., "Systematic review of validity testing in colonoscopy simulation", Surgical Endoscopy, Nov. 2012 (epub May 2012), 26(11), pp. 3040-3052.

(Continued)

*Primary Examiner* — Rene T Towa
(74) *Attorney, Agent, or Firm* — Bryce W. Burnham; Booth Udall Fuller, PLC

(57) ABSTRACT

The invention relates to human limb and joint movement pattern detection and analysis and is directed to warning systems for repetitive motion injuries and methods for warning a subject of movements at increased risk for repetitive use injuries, for example, using the warning systems. The invention tracks limb and joint movement of a subject during repetitive motion activities and can signal the subject to perform ergonomically safe movements.

10 Claims, 1 Drawing Sheet

(52) U.S. Cl.
CPC .... *A61B 5/7278* (2013.01); *A61B 2560/0223* (2013.01); *A61B 2562/0219* (2013.01); *A61B 2562/0223* (2013.01)

(56) References Cited

U.S. PATENT DOCUMENTS

| | | | | |
|---|---|---|---|---|
| 5,791,351 | A * | 8/1998 | Curchod | A61B 5/1121 600/587 |
| 6,059,576 | A * | 5/2000 | Brann | A61B 5/1116 434/247 |
| 6,487,906 | B1 * | 12/2002 | Hock | A61B 5/1126 73/379.01 |
| 7,070,571 | B2 | 7/2006 | Kramer et al. | |
| 7,503,878 | B1 * | 3/2009 | Amsbury | A61B 5/0002 482/1 |
| 2002/0170193 | A1 * | 11/2002 | Townsend | A61B 5/1116 33/512 |
| 2007/0032748 | A1 * | 2/2007 | McNeil | A61B 5/1038 600/595 |
| 2007/0250286 | A1 * | 10/2007 | Duncan | A61B 5/6833 702/139 |
| 2009/0024065 | A1 * | 1/2009 | Einarsson | A41D 13/1281 602/26 |
| 2009/0076418 | A1 * | 3/2009 | Jung | G16H 40/63 600/595 |
| 2010/0075806 | A1 | 3/2010 | Montgomery | |
| 2011/0257928 | A1 | 10/2011 | Cunningham | |
| 2012/0022884 | A1 * | 1/2012 | Chillemi | A61B 5/1121 705/2 |
| 2012/0158437 | A1 | 6/2012 | Little et al. | |
| 2013/0244211 | A1 * | 9/2013 | Dowling | G06F 19/3481 434/247 |

OTHER PUBLICATIONS

Asge Technology Committee, "Minimizing occupational hazards in endoscopy: personal protective equipment, radiation safety, and ergonomics", Gastrointestinal Endoscopy, Aug. 2010 (epub May 2010), 72(2), pp. 227-235.
Browne, A. et al., "A medical hand tool physical interaction evaluation approach for prototype testing using patient care simulators", Applied Ergonomics, May 2012 (epub Aug. 2011), 43(3), pp. 493-500.
Buschbacher, R., "Overuse syndromes among endoscopists", Endoscopy, 1994, 26(6), pp. 593-544.
Byun, Y. et al., "Procedure-related musculoskeletal symptoms in gastrointestinal endoscopists in Korea", World Journal of Gastroenterology, Jul. 2008, 14(27), pp. 4359-4364.
Craje, C. et al., "The effects of task and content on digit placement on a bottle", Experimental Brain Research, Jul. 2011 (epub May 2011), 212(1), pp. 119-124.
Drury, C., "Hand-held computers for ergonomics data collection", Applied Ergonomics, Jun. 1987, 18(2), pp. 90-94.
Fu, Q. et al., "Anticipatory Planning and Control of Grasp Positions and Forces for Dexterous Two-Digit Manipulation", Journal of Neuroscience, Jul. 2010, 30(27), pp. 9117-9126.
Hansel, S. et al., "Prevalence and Impact of Musculoskeletal Injury Among Endoscopists: A Controlled Pilot Study", Journal of Clinical Gastroenterology, May 2009, 43(5), pp. 399-404.
Hill, A. et al., "Assessing the realism of colonoscopy simulation: the development of an instrument and systematic comparison of 4 simulators", Gastrointestinal Endoscopy, Mar. 2012 (epub Feb. 2012), 75(3), pp. 631-640.e3.
Liberman, A. et al., "Injuries sustained by colorectal surgeons performing colonoscopy", Surgical Endoscopy, Dec. 2005 (epub Oct. 2005), 19(12), pp. 1606-1609.
Mohankumar, M. et al., "Characterization of right wrist posture during simulated colonoscopy: an application of kinematic analysis to the study of endoscopic maneuvers", Gastrointestinal Endoscopy, Mar. 2014 (epub Jan. 2014), 79(3), pp. 480-489.
O'Sullivan, S. et al., "Musculoskeletal Injuries among ERCP Endoscopists in Canada", Canadian Journal of Gastroenterology, Jun. 2002, 16(6), pp. 369-374.
Patent Cooperation Treaty, International Searching Authority, International Preliminary Report on Patentability and Written Opinion for PCT/US2015/030010, 6 pages, issued Nov. 15, 2016, opinion dated Aug. 12, 2015.
Patent Cooperation Treaty, International Searching Authority, International Search Report for PCT/US2015/030010, 3 pages, dated Aug. 12, 2015.
Shergill, A. et al., "Ergonomics and GI endoscopy", Jul. 2009 (epub Jun. 2009), 70(1), pp. 145-153.
Shergill, A. et al., "Pinch force and forearm-muscle load during routine colonoscopy: a pilot study", Gastrointestinal Endoscopy, Jan. 2009 (epub Dec. 2008), 69(1), pp. 142-146.
Shergill, A. et al., "Response to 'Call for Guidelines of Ergnomics in GI Endoscopy'", Gastrointestinal Endoscopy, Jun. 2010, 71(7), p. 1333.
Sheth, A. et al., "Call for guidelines on ergonomics in GI endoscopy", Gastrointestinal Endoscopy, Jun. 2010, 71(7), p. 1333.
Siegel, J., "Risk of Repetitive-Use Syndromes and Musculoskeletal Injuries", Techniques in Gastrointestinal Endoscopy, Oct. 2007, 9(4), pp. 200-204.
Van Tulder, M, et al., "Repetitive strain injury", Lancet, May 2007, 369(9575), pp. 1815-1822.
Harvin, Glenn, "Review of Musculoskeletal Injuries and Prevention in the Endoscopy Practitioner", J Clin Gastroenterol, 48(7):590-594 (2014).
Herman, Daniel C. et al., "The Effects of Feedback with and without Strength Training on Lower Extremity Biomechanics", The American Journal of Sports Medicine, 37(7):1301-1308 (2009) (Abstract only).
Lieberman, Jeff et al., "TIKL: Development of a Wearable Vibrotactile Feedback Suit for Improved Human Motor Learning", IEEE Transactions in Robotics, 23(5):919-926 (2007) (Abstract only).
Myer, Gregory D. et al., "Real-time assessment and neuromuscular training feedback techniques to prevent ACL injury in female athletes", Strength Cond J., 33(3):21-35 (Jun. 1, 2011).
Myer, Gregory D. et al., "Augmented Feedback Supports Skill Transfer and Reduces High-Risk Injury Landing Mechanics: A Double-Blind, Randomized Controlled Laboratory Study", The American Journal of Sports Medicine, 41(3):669-677 (Jan. 31, 2013) (Abstract only).
Onate, James A. et al., "Augmented Feedback Reduces Jump Landing Forces", Journal of Orthopaedic & Sports Physical Therapy, 31(9):511-517 (2001).
Peper, Erik et al., "The Integration of Electromyography (SEMG) at the Workstation: Assessment, Treatment, and Prevention of Repetitive Strain Injury (RSI)", Applied Psychophysiology and Biofeedback, 28:167-182 (2003) (Abstract only).
Sasson, Joseph R. et al., "The Effects of Training, Feedback, and Participant Involvement in Behavioral Safety Observations on Office Ergonomic Behavior", Journal of Organizational Behavior Management, 24(4):1-30 (2008) Abstract only).
Sigrist, Roland et al., "Augmented visual, auditory, haptic, and multimodal feedback in motor learning: A review", Psychon Bull Rev, 20:21-53 (2013).

* cited by examiner

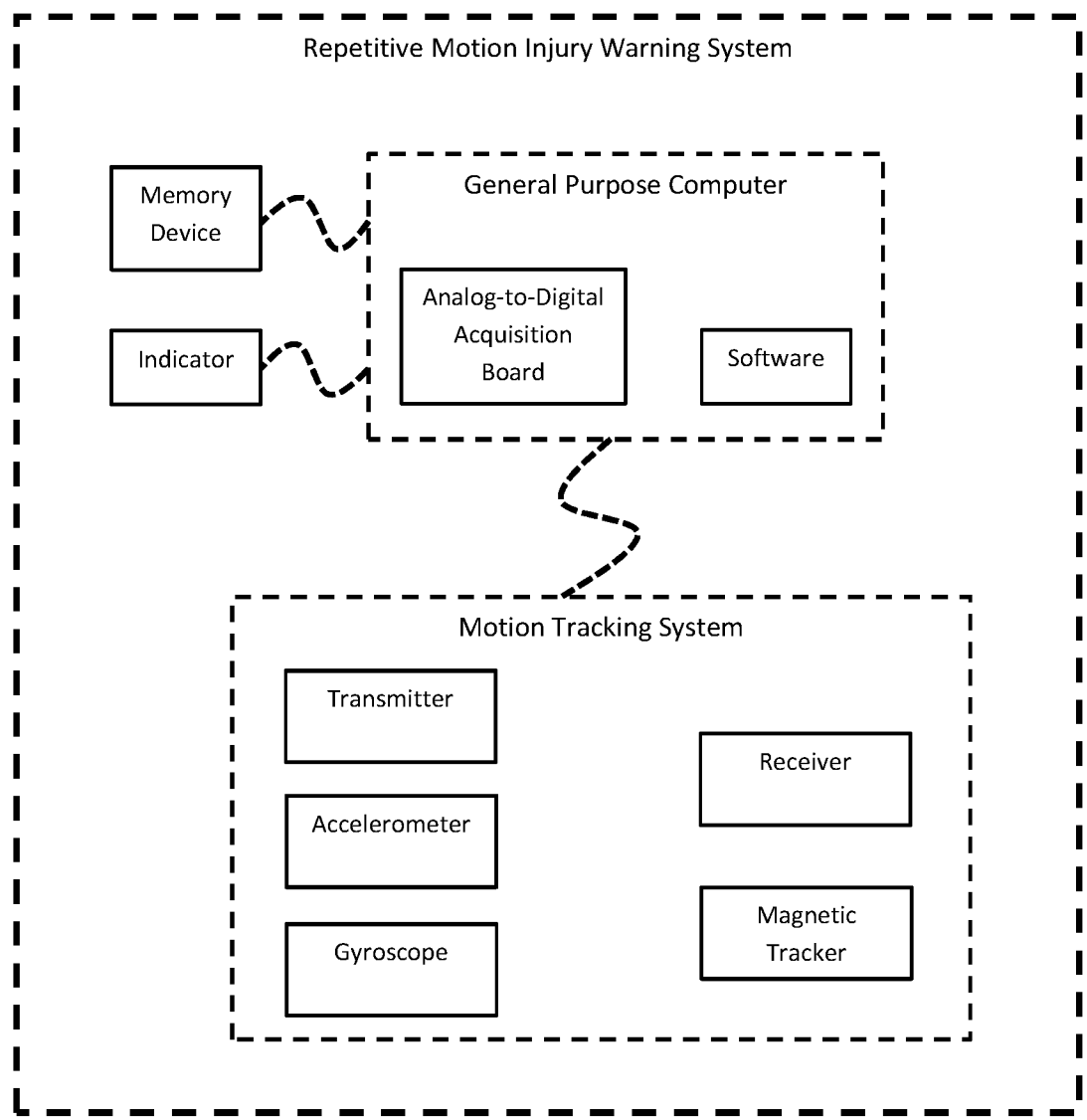

REPETITIVE MOTION INJURY WARNING SYSTEM AND METHOD

CROSS REFERENCE TO RELATED APPLICATIONS

This document claims the benefit of U.S. Provisional Patent Application 61/991,199, filed on May 9, 2014, the contents of which are hereby incorporated by reference thereto for all purposes in its entirety.

TECHNICAL FIELD

This application relates to limb and joint movement pattern detection and analysis. In particular, the invention provides a system and method for tracking limb and joint movement of a subject during repetitive motion activities, for example, during endoscopic procedures, and can provide important information of how to assist the subject performing ergonomically safe movements.

BACKGROUND OF THE INVENTION

Overuse syndrome is a disorder where a certain part of the body is damaged by repeatedly overusing it or subjecting it to too much stress. The strain that causes overuse syndrome occurs when a body part is improperly used over time. The term overuse syndrome identifies a large group of conditions, including tendonitis, bursitis, carpal tunnel syndrome, patellofemoral pain, IT band syndrome, and plantar fasciitis.

Repetitive strain injuries are a type of overuse syndrome that affects bones, muscles, tendons, nerves and other structures of the musculoskeletal and nervous systems. It develops when small injuries occur repeatedly from repetitive tasks, forceful exertions, vibrations, mechanical compression (impact on hard surfaces), or sustained or awkward positions.[1]

With regard to repetitive physical activities, when muscles are contracted at static joint positions for extended periods of time, they are not able to relax rhythmically. This results in less oxygenated blood flow to the tissues.[2]

Endoscopy procedures include these risk factors. Endoscopy procedures involve repeated pinching or gripping of the endoscope and pushing, pulling, and torqueing of the insertion tube in potentially awkward postures.[3]

A. Prevalence of Musculoskeletal Injuries Among Endoscopists

Studies have highlighted overuse injuries in endoscopists. Survey-based studies have estimated a prevalence of musculoskeletal symptoms ranging from 37% to 89%.[5] Common regions of pain were the left thumb, the right wrist, the neck, and the back.[5] One survey investigating the prevalence of diagnosed upper extremity disorders found that 40% of 88 surveyed endoscopists had already had a diagnosis of an upper extremity disorder, mostly in the hand-wrist area.[4]

The studies document an association between endoscopy and musculoskeletal complaints, and they show a consistently high prevalence of musculoskeletal complaints among endoscopists.[5] Surgery and time off work was required in a minority of those surveyed.[5]

Gastroenterologists spend 43% of their time performing endoscopy procedures, which averages to about 34 procedures per week.[4] It is estimated that after 10 years of exposure, approximately 10% of endoscopists would be expected to have an upper extremity musculoskeletal disorder.[4]

B. Mechanism of Injury During Endoscopy procedures

During endoscopy, the left hand grips and stabilizes the control section, the left thumb manipulates the control dials, the right hand pinches or grips the insertion tube, and the right arm pushes, pulls, and applies torque to the endoscope. These activities may require extreme or prolonged wrist flexion or extension and/or radial or ulnar deviation during endoscopy that can decrease pinch or grip strength.[5]

As such, potential mechanisms of overuse injury include: (1) repetitive hand activities; (2) high pinch forces; and (3) sustained awkward postures.[4] The risk of injury also appears to be related to endoscopy volume,[5] the amount of time the endoscopy is used (i.e., the type and/or complexity of the endoscopy procedure),[4] and the design of the instruments.[5]

The different types of endoscopy procedures differ in the levels of risk. Upper endoscopy or EGD is of shorter duration than the others, which minimizes the exposure of endoscopists to significant loads. As such, the primary concern with EGDs is maintaining a neutral body posture.[5]

Colonoscopy with or without biopsy is typically longer in duration and requires more time to advance and withdraw the instrument compared with EGD. Thus, there is more repetition, more use of high forces when maneuvering the colonoscope tip, and longer use of awkward postures. It is believed that the left wrist extensors (which stabilize the instrument control section) are at greatest risk of injury.[5] In a case study, "colonoscopist's thumb" (wrist tendonitis at the first extensor compartment) was attributed to left-thumb strain because of repeated turning of the dials of the control section of the colonoscope.[5]

A study of surgeons who performed colonoscopy reported that 39% of surgical endoscopies had at least one injury or pain related to colonoscopy, whereas the risk increased to 47% among surgeons who performed more than 30 colonoscopies per week. The left thumb, finger and hand injuries were attributed to turning the control dials and gripping the colonoscope handle, and most of the right upper-extremity injuries were attributed to torqueing of the colonoscope.[5] Gastroenterologists perform an average of 12 EGDs and 22 colonoscopies per week.[5]

Studies document potentially high peak forces during colonoscopy that may reach levels associated with an increased risk of musculoskeletal injury of the thumb and wrist. Mean forces throughout colonoscopy appear low. The greatest loads occur during insertion, especially into the sigmoid colon, presumably because of looping. Only one study evaluated EMG activity of the distal upper extremity during colonoscopy, and loads of the left-wrist extensors, the right-wrist extensors, and the left-thumb extensors approached levels at which general controls or surveillance was warranted.[5]

Endoscopic retrograde cholangiopancreatography (ERCP) combines endoscopy and fluoroscopy to diagnose and treat certain problems of the biliary or pancreatic ductal systems. ERCP uses an elevator, which increases the left-thumb load.[5] In addition, ERCP involves the static load of the lead apron.[5]

Endoscopic ultrasound (EUS) or echo-endoscopy combines endoscopy and ultrasound to obtain images of the internal organs in the chest and abdomen. The older, mechanical echo-endoscopes have their motor mounted on the control handle. These models are therefore much heavier than electric echo-endoscopes and produce increased static loads on the left hand and wrist. As such, endoscopists should use the electronic echo-endoscopes whenever possible.[4]

Balloon-assisted enteroscopy also is associated with prolonged procedure times and extensive right arm repetitive maneuvers and may predispose the endoscopist to injury.[4]

The basic shape and design of endoscopes have not changed for over 20 years. Current endoscope design requires mechanical application of force by the left hand digits to the control dials to deflect the insertion-tube tip during examination. Although the majority of the force is applied by the left thumb, the digits of the left hand may provide additional force if the endoscopist has a large enough hand. Movement of the endoscope tip also can be achieved by application of torque to the insertion tube by the right hand and arm coupled with up-down tip deflection by the left hand.

In addition to the torque and push-pull forces applied by the right hand, the right hand is also important for threading tools through the biopsy channel. One prior report describes "biliary endoscopist's knuckle," a traumatic arthritis of the metacarpophalangeal joint attributed to repeated high-force gripping to push large-caliber prostheses through biliary and pancreatic strictures.

For all types of endoscopy procedures, sustained awkward postures occur if the video monitor is placed too high or off to the endoscopist's side, causing extension or rotation of the spine, and/or if the patient's gurney is not adjusted to an optimal height.[5]

One study concluded that endoscopists tend to spend a significant amount of time at the extremes of wrist joint range of motion. It is felt that if repetitive wrist motion to its range-of-motion extreme were reduced or eliminated, then overuse injuries could be minimize or prevented.[2]

C. Attempts to Address Endoscopists' Occupational Risks

Attempts to date of addressing an endoscopists' high risk for overuse injury include ergonomically designed surgery suites, load reducing maneuvers, muscle recovery rest periods, fitness, sharing the physical load with a second endoscopist and re-designing key equipment.

(1) Ergonomics

As one author put it, ergonomics is a most neglected aspect of both the training and the practice of GI endoscopy.[6] Today, gastroenterologists are facing rigorous training, an increasing demand for endoscopy, and decreasing payment. This is driving practices toward more endoscopy procedures in order to meet the demand and payment goals. This is likely to escalate occupational injuries.[6]

Basic ergonomic principles have been suggested to address the problem of developing repetitive strain injuries, such as neutral wrist, neck, and shoulder postures during endoscopy and keeping hand forces low.[5] Specifically, one can maintain a neutral posture by ensuring that the monitor is at or below eye level and the patient gurney is at elbow level.[4] It has been further suggested that fellows and practicing endoscopists receive training on how to protect themselves from injury.[7]

(2) Load Reducing Measures

Additionally, some researchers have developed maneuvers aimed at reducing hand or wrist loads. A technique called the "left hand shaft grip" has been described to provide assistance to the left thumb during sharp turns or difficult polypectomies. A variation on this is the "pinkie maneuver." These maneuvers only apply if a procedure requires additional use of the right-left dial to negotiate a turn.[5]

A two-handed technique has been postulated to reduce the risk of left-thumb injury but has not been formally studied, and it is in general not thought to be as efficient as the one-handed technique to control the dials.[5]

With respect to the additional load of a lead apron used in ERCP, some suggest a two-piece lead apron offers a theoretical advantage because the load can be more evenly distributed between the spine and pelvis.[4]

(3) Rest and Fitness

Some have suggested that endoscopists should take a break between procedures to allow heavily used muscle groups to recover.[5] Others have stressed the importance of fitness and the maintenance of a normal body mass index to avoid musculoskeletal injury.[8]

(4) Load Sharing

It has been suggested that risk of injury may be reduced if endoscopies were performed with two people, as opposed to the traditional one-person endoscopy.[5] A study conducted to assess the potential for upper extremity biomechanical overload inadvertently dispelled this notion. The researchers used the Occupational Repetitive Actions (OCRA) index, which is an ergonomic risk assessment tool that ranks a job's repetitive tasks as follows: (1) no risk; (2) low risk; and (3) risk. Six endoscopists were evaluated during two different insertion methods: one-person versus two-person endoscopy. For all procedures, the endoscope was held by the subject's left hand, and the right hand was used to turn the dials. This study found slight exposure levels for the left upper limb and medium to high exposure levels for the right upper extremity, with no difference in risk between one-person and two-person endoscopy.[4]

(5) Re Designed Endoscopes

New, theoretically ergonomically favorable endoscopic devices are currently under development. The goal would be to eliminate the need for an endoscopist to maneuver the colonoscope through the colon because it is self-propelled and either self-navigating or guided by a joystick. These devices, however, are not yet commercially available and are untested.[4]

No consideration to date has been given in endoscopic design to accommodate variability in hand size or the difference in hand sizes between men and women. A pilot study, however, evaluated the use of an angulation dial adapter for hand spans. Although no significant difference was found in procedure time or ease of procedure, retroflexion was rated significantly easier with the adapter by all endoscopists. The investigators concluded that further evaluation of endoscope design may reduce hand fatigue and injury, given that the angulation dial showed a trend toward decreased procedure time in physicians with small hands.[5]

SUMMARY OF THE INVENTION

The invention is directed to a repetitive motion injury warning system. The warning system generally includes a general-purpose computer, wherein the general-purpose computer has at least an analogue-to-digital acquisition board and a software operating on the general-purpose computer. The warning system also typically includes a motion tracking system configured to detect the motion and position of a body part of a subject, wherein the information on the motion and position of the body part of the subject is loaded to the general-purpose computer and the software processes the information on the motion and position the body part of the subject to compute a body part angle.

The software operating on the general-purpose computer determines an individualized safe range and/or an individualized risky range of the body part angle based on the information on the motion and position the body part of the subject. In some implementations wherein the information on the motion and position the body part from a plurality of subjects is loaded to the general-purpose computer, the software operating on the general-purpose computer determines a generic safe range and/or a generic risky range of the body part angle based on the information on the motion and position the body part of the subject. The software operating on the general-purpose computer may also determine sub-ranges of the safe range and/or risky range of the body part angle based on the information on the motion and position the body part of the subject or the plurality of subjects.

In some embodiments, the software operating on the general-purpose computer signals the general-purpose computer to emit an indicator that corresponds with the individualized or generic range or sub-range of the body part angle. For example, in some aspects, the indicator is a warning signal when the body part angle falls within the individualized or generic risky range.

In some embodiments, the motion tracking system comprises a receiver, wherein the receiver is attached to the body part of the subject. The body part of the subject is selected from the group consisting of a hand, an arm, a forearm, or any combinations thereof. In some aspects, the motion tracking system further comprises a transmitter, an accelerometer, a gyroscope, and/or a magnetic tracker.

The invention also provides methods for warning a subject of movements at increased risk for causing repetitive use injuries using the warning system described above.

In one implementation, the methods comprise tracking in real-time movement of the body part while the subject is engaged in an activity of interest using the motion tracking system; determining in real-time the angle of the body part while the subject is engaged in an activity of interest using the software operating on the general-purpose computer; comparing continuously in real-time the angle of the body part with a risky range of motion of the body part and a safe range of motion of the body part; and issuing a warning signal when the angle of the body part is within the risky range motion of the body part. The risky range motion of the body part is the two extremes of a range of body part angles, and the safe range is the central range of the range of body part angles. In some aspects, the range of body part angles is determined from a plurality of subjects.

In another implementation, the methods comprise calibrating a range of motion of a body part of the subject comprising: defining an individualized risky range of motion of the body part and an individualized safe range of motion of the body part using the software operating on the general-purpose computer, wherein the individualized risky range is the two extremes of the range of body part angles and the individualized safe range is the central range of the range of body part angles; tracking in real-time movement of the body part while the subject is engaged in an activity of interest using the motion tracking system; determining in real-time the angle of the body part while the subject is engaged in an activity of interest using the software operating on the general-purpose computer; comparing continuously in real-time the angle of the body part with the individualized risky range and the individualized safe range; and issuing a warning signal when the angle of the body part is within the individualized risky range. In some aspects, the calibrating step comprises moving the body part of the subject through the body part's full range of motion; tracking the range of motion of the body part using the motion tracking system; and determining the angle of the body part through its full range of motion to generate a range of body part angles of the subject using the software operating on the general-purpose computer.

In some embodiments, the methods further comprise computing a quality metric showing how many warning signals were given while the subject was engaged in the activity of interest; computing a score showing the overall quality of the activity in terms of risk for repetitive use injuries; and/or defining sub-ranges of the risky range and sub-ranges of the safe range. In some aspects where the methods comprise computing a score, the individualized or generic risky range and/or safe range and/or the sub-ranges thereof are assigned a quantifiable value from which the score is calculated.

BRIEF DESCRIPTION OF THE DRAWINGS

FIG. 1 illustrates a schematic view of an embodiment of a repetitive motion injury warning system.

DETAILED DESCRIPTION OF THE INVENTION

The verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" refers to humans and other vertebrates. In some embodiments, the subject is a human.

The invention provides, among other things, a warning system for repetitive motion injuries. This system may be used to train users (e.g. subjects) to use equipment and instruments in an ergonomically safe manner. The invention may be adapted to any joint movement believed to be the cause of overuse injury in any occupation or activity. Thus the invention could result in a novel way to train endoscopists worldwide and become the gold standard for endoscopy training as well as, potentially, other types of medical procedures that are associated with a high incidence of overuse injuries. The warning system of the invention comprises a general-purpose computer, a software, and a motion tracking system.

The motion tracking system is configured to detect the motion and position of a body part of a subject. The body part of the subject may be, for example, a joint, a limb, parts of a limb, a hand, a foot, a finger, neck, waist, or back. In some aspects, the motion tracking system comprises a receiver, wherein the receiver is attached to the body part of the subject. In one embodiment, receivers are attached to body parts of the subject such that joint angles (e.g. body part angles) corresponding to the body parts may be determined by the motion and position of the body parts. The motion tracking system may be an inertial motion/measurement unit (IMU) comprising accelerometers, gyroscopes, and/or magnetic trackers. In some aspects, the IMU may consist of accelerometers, gyroscopes and magnetic trackers. Accelerometers measure acceleration, while gyroscopes measure orientation. Magnetic trackers allow the user to avoid needing a clear line of sight between receivers and transmitters. The motion tracking system may be wired or wireless. In one embodiment, the motion tracking system is worn on the arm, forearm, and hand of the subject.

Information on the motion and position of the body part of the subject is loaded to the general-purpose computer and the software processes the information on the motion and position the body part of the subject to compute a body part angle. The general-purpose computer has an analog-to-digital data acquisition board. For example, the general-purpose computer may be a desktop, a laptop, or a mobile device such as a tablet or smartphone. The software, which operates on the general-purpose computer, computes both online and offline, Calculation results may be used for calibration and display during and after the activity that may produce repetitive motion injuries.

In some aspects, the software performs additional functions, such as determining a safe range of body part angle and a risky range of body part angle (or a range of body part angle that is potentially unsafe/leading to musculoskeletal injuries). The safe risky ranges of body part angle may be individualized, which is calculated from the motion of one subject and applied to that subject. In other aspects, the safe and risky ranges of body part angle may be calculated from the motion of a plurality subject to result in generic ranges that may be applied to general population of subjects. For example, the information on the motion and position of the body part from a plurality of subjects would be representative of the general population of subjects. The software may also determine sub-ranges of the safe and risky ranges of body part angle.

In some embodiments, the warning system may emit an indicator that corresponds with the individualized or generic risky range and/or safe range and/or sub-ranges thereof as the system tracks the movements of a subject performing an activity that may result in repetitive use injury. In some aspects, the indicator may be a warning signal when the subject's body part angle being measured falls within the individualized or generic risky range.

The warning system may also produce evaluations of a subject's movement while performing an activity that may result in repetitive use injury. In one aspect, the quality metric for the evaluation may be the number of warning signals the subject received during the performance of the activity. The evaluations may also be a score that reveals the overall quality of the activity in terms of risk for repetitive use injuries. For example, the individualized or generic risky range and/or safe range and sub-ranges thereof may be assigned a quantifiable value, and a score may be calculated from the quantifiable value that reflects whether the performed activity was at the risky range for repetitive use injury. In some implementations, the score may also determine how risky the performed activity was at for repetitive use injury.

The invention seeks to address the matter from a different perspective: i.e., signal endoscopists that they are in a posture that places them at risk of injury. It is a system that uses a motion tracking system and general-purpose computer software to provide online and offline feedback to the endoscopist. In some embodiments, the invention is capable of signaling the endoscopist when he/she is moving in a pattern that may lead to overuse injuries for the ultimate purpose of training users to move in a way that does not strain joints and muscles (i.e., moving within the acceptable range of motion).

The concept of providing feedback to train users to perform ergonomically safe movements is novel. The feedback mechanism: (a) defines ranges of joint range of motion based on "safe" (safe range of the body part angle) versus "potentially unsafe/leading to musculoskeletal injuries" (risky range of the body part angle); and (b) provides feedback so that the endoscopist can practice and learn ergonomically correct movement patterns. No feedback system exists that is based on the notion of providing feedback related to joint range of motion.

Most feedback-driven devices for surgery maneuver training are designed to signal either success or failure, based on specific movement metrics, through scores, sounds and so forth. The movements being measured are not body movements, but rather the trainee's movement of the instruments during a simulation. Further, the movement data collected from the trainee is compared to and/or measured against data collected from seasoned professionals performing the same simulated procedure. As such, these feedback systems all aim solely at improving performance, rather than preventing musculoskeletal injuries as targeted by the proposed invention.

For example, U.S. Pat. No. 5,275,174 (published Jan. 4, 1994) to Cook describes a method and means of assessing repetitive strain injury. The patent states that repetitive strain injuries are difficult to diagnose and treat due to the lack of objective assessment tools. To that point in time, practitioners had to rely on the patient's subjective responses, which may not be reliable. The patent assessed the physiological status of the joint-tendon-muscle system of the wrist by having the subject rotate his/her wrist in a specified way against two levels of resistance. Sensors were placed on the muscles in the forearm controlling the movement. Electrical activity associated with muscle contraction was recorded and compared to norms. Thus, the invention of this patent measures muscle activity, not joint movement. The patent is limited to measuring a single, specific movement for purposes of injury assessment. It does not and cannot be used to measure the joint movements throughout a medical procedure. Finally, the invention does not provide real-time feedback.

U.S. Pat. No. 7,070,571 (published Jul. 4, 2006) to Kramer et al. describes full- and half-body motion tracking suits intended for purposes of creating general-purpose computer-generated animation, biomechanical applications, and evaluating the general ergonomic fitness of activities. The suit contains a series of links coupled to hinge joints. The hinge joints are strategically positioned to move in relation to a body part. "Bend sensors" are positioned over the hinge joints and provide positional data relative to the terminal links. The patent mentions that one application of the body suit might be measuring the upper body movements of a typical clerical worker over a full workday in order to assess the role of various activities causing repetitive strain injury. The suit, however, merely sends a position signal via the bend sensors. It does not analyze the data, compare it to other data, provide feedback, or perform the other functions of the invention.

Methods of Use

The invention may be used to train subjects to avoid movements at increased risk for repetitive use injuries. For example, the example endoscopists, to avoid spending any significant time in positions that are likely to lead to repetitive strain injuries. This is accomplished by warning a subject when the subject performs movements that result in increased risk for repetitive use injuries using the warning system of the application.

The methods for warning a subject of movements at increased risk for causing repetitive use injuries may comprise calibrating a range of motion of a body part of the subject. In some implementations, calibrating the range of motion of a body part of the subject may comprise moving the body part of the subject through the body part's full range of motion and tracking the range of motion of the body part using the motion tracking system. As the motion tracking system loads the information on the range of motion and position of the body part to the general-purpose computer, the method further comprises determining the angle of the body part through its full range of motion to generate a range of body part angles of the subject using the software operating on the general-purpose computer. In some embodiments, the software operating on the general-purpose computer defines a risky range of motion of the body part and a safe range of motion of the body part. The individualized risky range is the two extremes of the range of body part angles, which represents the riskiest joint angle, and the individualized safe range is the central range of the range of body part angles, which represents the safest joint angle. The risky range of motion of the body part or the riskiest joint angle are positions that maximally strain the joint capsule, ligaments, tendons, and/or muscles.

In some implementations, the general-purpose computer or the software operating on the general-purpose computer defines sub-ranges of the risky range and safe range. Sub-ranges may be defined by section of the body part angle that is in 5% increments of the safe range or the risky range. In some implementations, ranges and sub-ranges may be defined by set percentage increments determine from the full range of motion of a particular body part. For example, the safe range may be the ±30% from the middle of the range of the body part angles while the risky range is anywhere beyond that range. In another example, the safe range may be ±30% from body part angle of that body part in a relaxed state while the risky range is anywhere beyond that range. In other implementations, the risky and safe ranges may be defined by set degree increments from the center of the safe range. For example, the safe range may be the ±30° from the middle of the range of the body part angles while the risky range is anywhere beyond that range. In another example, the safe range may be ±30° from body part angle of that body part in a relaxed state while the risky range is anywhere beyond that range.

Calibrating the range of motion of the body part of the subject enables individualized analysis of the movements that increase that subject's risk for repetitive use injury. However, the risky range and the safe range may be determined using the information on the range of motion and position of the body part collected from a plurality of subjects. The plurality of subjects should be representative of the general population of subjects. The resulting generic risky range and safe range determined from a plurality of subjects may be stored on the software or the general-purpose computer. Accordingly, the methods for warning a subject of movements at increased risk for causing repetitive use injuries may not require determining the risky range and safe range of the body part angle for each individual subject and only require the training steps.

The training steps of the methods for warning a subject of movements at increased risk for causing repetitive use injuries comprise tracking in real-time movement of the body part while the subject is engaged in an activity of interest using the motion tracking system; determining in real-time the angle of the body part while the subject is engaged in an activity of interest using the software operating on the general-purpose computer; comparing continuously in real-time the angle of the body part with the individualized risky range and the individualized safe range; and issuing a warning signal when the angle of the body part is within the individualized risky range.

In some implementations, the training steps of the methods for warning a subject of movements at increased risk for causing repetitive use injuries further comprises computing a quality metric showing how many warning signals were given while the subject was engaged in the activity of interest. In some aspects, the methods may further comprise computing a score showing the overall quality of the activity in terms of risk for repetitive use injuries. In such embodiments, the risky range, safe range, and/or the sub-ranges thereof are assigned a quantifiable value from which the score is calculated.

The invention is further illustrated by the following examples that should not be construed as limiting. The contents of all references, patents, and published patent applications cited throughout this application, as well as the FIGURES, are incorporated herein by reference in their entirety for all purposes.

Examples

1. Application for Endoscopists, Wherein the Activity of Interest is the Performance of Endoscopy Procedures The invention may be used to train endoscopists to avoid spending any significant time in positions that are likely to lead to repetitive strain injuries. This is accomplished by first measuring the range of motion of each upper limb major joint (shoulder, elbow, and wrist). Second, using the measurement, define two parameters: (1) the center of the joint range of motion, which represents the safest joint angle; and (2) the two extremes of the joint range of motion, which represent the riskiest joint angles, as said positions, by definition, maximally strain the joint capsule, ligaments, tendon and muscles. Third, define the sub-ranges of motion between the above two ranges. Fourth, the center and extreme position parameters are entered in the software.

Next, the endoscopists perform a procedure using an endoscopy simulator, during which the joint angle data are recorded in real time and continuously compared with the parameters. When one or more joint angles approaches an extreme position, a warning signal will be discharged, in the form of either a visual display, sound or both (e.g., a red light that goes on/off together with a sound at 2 Hz frequency). The endoscopist is then instructed to relax and use slightly different postures. The goal is to minimize the number and duration of the warning signals during the entire procedure. At the end of the procedure, the software computes a quality metric showing how many warning signals were given during the procedure and a score summarizing the overall quality—in terms of straining the joint(s) of the user—of the entire procedure. The software can replay the procedure while superimposing the worst scores, allowing the user to see in what positions and during which movements (what part of the body) he/she tended to strain his/her joints the most. Thus, the present intervention serves as a primer for use in subsequent procedures.

REFERENCES 1. van Tulder, Maurits, et al., "Repetitive strain injury," Lancet, May 2007, pp. 1815-22, Vol. 369, No. 9575.
2. Mohankumar, Deepika, et al., "Characterization of right wrist posture during simulated colonoscopy: an application of kinematic analysis to the study of endoscopic maneuvers," Gastrointest. Endosc., 2014, Vol. 79, No. 3.
3. Shergill, Amandeep K., et al., "Pinch force and forearm-muscle load during routine colonoscopy: a pilot study," Gastrointest. Endosc., January 2009, pp. 142-46, Vol. 69, No. 1.

4. Predroza, Marcos C., et al., "Minimizing occupational hazards in endoscopy: Personal protective equipment, radiation safety and ergonomics," Gastrointest. Endosc., August 2010, pp. 227-35, Vo. 72, No. 2.
5. Shergill, Amandeep K., et al., "Ergonomics and GI endoscopy," Gastrointest. Endosc., 2009, pp. 145-53, Vol. 70, No. 1.
6. Sheth, Ankur, et al., "Call for Guidelines of Ergonomics in GI Endoscopy," Gastrointest. Endosc., June 2010, p. 1333, Vol. 71, No. 7.
7. Shergill, Amandeep K., et al., "Response to 'Call for Guidelines of Ergonomics in GI Endoscopy,'" Gastrointest. Endosc., June 2010, p. 1333, Vol. 71, No. 7.
8. Siegel, Jerome H., "Risk of Repetitive-Use Syndromes and Musculoskeletal Injures," Techniques Gastrointest. Endosc., pp. 200-04, Vol. 9, No. 4.

What is claimed:

1. A method for warning an endoscopist of increased risk for hand and wrist repetitive motion injuries for endoscopy procedures, comprising:
    calibrating a range of motion of a hand and wrist of the endoscopist wherein the calibrating step comprises:
        moving the hand and wrist of the endoscopist through the hand and wrist's full range of motion;
        tracking the range of motion of the hand and wrist using a motion tracking system; wherein the motion tracking system comprises at least one of an accelerometer, a gyroscope, or a magnetic tracker; and
        determining the angle of the hand and wrist through the full range of motion of the hand and wrist to generate a range of body part angles of the endoscopist using a software operating on a general-purpose computer;
    defining an individualized risky range of motion of the hand and wrist and an individualized safe range of motion of the hand and wrist using the software operating on the general-purpose computer, wherein the individualized risky range is the two extremes of the range of body part angles and the individualized safe range is the central range of the range of body part angles;
    tracking in real-time with the motion tracking system movement of the hand and wrist while the endoscopist is engaged in an endoscopy using the motion tracking system;
    determining in real-time the angle of the hand and wrist while the endoscopist uses instruments for the endoscopy using the software operating on the general-purpose computer;
    identifying continuously in real-time when the angle of the hand and wrist is within the individualized risky range and the individualized safe range;
    issuing a real-time warning signal when the angle of the hand and wrist is within the individualized risky range; and
    replaying a procedure performed by the endoscopist after the procedure is completed, allowing the endoscopist to see both procedure performance for the patient and in what positions and during which movements the endoscopist tended to most strain joints.

2. The method of claim 1, further comprising computing a quality metric showing the number of warning signals issued while the endoscopist was engaged in the endoscopy.

3. The method of claim 1, further comprising defining sub-ranges of the individualized risky range and sub-ranges of the individualized safe range.

4. The method of claim 1, further comprising computing a score showing the overall quality of the endoscopy in terms of risk for repetitive use hand and wrist injuries, wherein at least one of the individualized risky range, the individualized safe range, or sub-ranges thereof are assigned a quantifiable value from which the score is calculated.

5. The method of claim 1, wherein replaying the endoscopy procedure performed by the endoscopist further comprises superimposing worst scores.

6. A method for warning an endoscopist of movements at increased risk for hand and wrist repetitive use injuries for endoscopy procedures, comprising:
    tracking movement of the hand and wrist in real-time using a motion tracking system while the endoscopist is engaged in an endoscopy procedure; wherein the motion tracking system comprises at least one of an accelerometer, a gyroscope, or a magnetic tracker;
    determining the angle of the hand and wrist in real-time using a software operating on a general-purpose computer while the endoscopist is engaged in the endoscopy procedure;
    identifying continuously in real-time when the angle of the hand and wrist is within a risky range of motion of the hand and wrist and a safe range of motion of the hand and wrist, wherein the risky range of motion of the hand and wrist is the two extremes of a range of hand and wrist angles and the safe range is the central range of the range of hand and wrist angles, wherein the range of hand and wrist angles is determined from the individual endoscopist;
    comparing continuously in real-time the angle of the endoscopist's hand and wrist with an individualized safe range, the individualized safe range derived by detecting and monitoring full range of motion of the endoscopist's hand and wrist;
    issuing a warning signal in real-time when the angle of the hand and wrist is within the risky range of motion of the hand and wrist; and
    further comprising replaying an endoscopy procedure performed by the endoscopist allowing the endoscopist to see in what positions and during which movements the endoscopist tended to most strain joints.

7. The method of claim 6, further comprising computing a quality metric showing the number of warning signals issued while the endoscopist was engaged in the endoscopy.

8. The method of claim 6, further comprising defining sub-ranges of the risky range and sub-ranges of the safe range.

9. The method of claim 8, further comprising computing a score showing the overall quality of the activity in terms of risk for repetitive use injuries, wherein one or more of the risky range, the safe range, the sub-ranges of the risky range, or the sub-ranges of the safe range are assigned a quantifiable value from which the score is calculated.

10. The method of claim 6, wherein replaying the endoscopy procedure performed by the endoscopist further comprises superimposing worst scores and serves as a primer for subsequent procedures to be performed by the endoscopist.

* * * * *